United States Patent
Mizuki

(10) Patent No.: US 9,738,451 B2
(45) Date of Patent: Aug. 22, 2017

(54) CONTAINER SUPPLY UNIT AND AUTOMATED ANALYZER

(71) Applicants: JEOL Ltd., Tokyo (JP); Fujirebio Inc., Tokyo (JP)

(72) Inventor: Nakamura Mizuki, Tokyo (JP)

(73) Assignees: JEOL Ltd., Tokyo (JP); Fujirebio Inc., Tokyo (JP)

( * ) Notice: Subject to any disclaimer, the term of this patent is extended or adjusted under 35 U.S.C. 154(b) by 0 days.

(21) Appl. No.: 15/310,220

(22) PCT Filed: May 7, 2015

(86) PCT No.: PCT/JP2015/063236
§ 371 (c)(1),
(2) Date: Nov. 10, 2016

(87) PCT Pub. No.: WO2015/174326
PCT Pub. Date: Nov. 19, 2015

(65) Prior Publication Data
US 2017/0152109 A1    Jun. 1, 2017

(30) Foreign Application Priority Data

May 14, 2014  (JP) ................. 2014-100075

(51) Int. Cl.
*B65G 47/24*   (2006.01)
*B65G 17/12*   (2006.01)
(Continued)

(52) U.S. Cl.
CPC ............ *B65G 17/12* (2013.01); *B65G 17/32* (2013.01); *B65G 47/14* (2013.01); *G01N 35/04* (2013.01);
(Continued)

(58) Field of Classification Search
CPC ........ B65G 17/12; B65G 17/32; B65G 47/24; B65G 47/26
(Continued)

(56) References Cited

U.S. PATENT DOCUMENTS

| 2,954,862 A | * | 10/1960 | Clark | ............. B65G 17/12 198/396 |
| 3,712,451 A | * | 1/1973 | Vignon | ............ B65H 67/061 198/397.01 |

(Continued)

FOREIGN PATENT DOCUMENTS

| FR | 2564064 A1 | 11/1985 | |
| JP | 3-259815 | * 11/1991 | ............. B65G 47/24 |

(Continued)

*Primary Examiner* — James S Bidwell
(74) *Attorney, Agent, or Firm* — The Webb Law Firm

(57) ABSTRACT

A container supply unit and an automated analyzer in which anomalous orientations of containers ejected from a container (cuvette) ejection part can be prevented. This container supply unit has a container storage part, a container ejection part, and a container alignment part. The container ejection part includes a circular belt, placement members provided on said circular belt, and a belt rotation mechanism. The belt rotation mechanism rotates the circular belt in an R direction, forming an outward leg along which the placement members move upwards and a return leg along which the placement members move downwards. The placement members carry containers placed thereon on the outward leg and eject said containers to the container alignment part between the outward leg and the return leg. The top of each placement member during the outward leg comprises the following: a first inclined surface that is sloped upwards from one end, on the circular-belt side, towards the other end; and a second inclined surface that is sloped downwards from one end, which connects to the first inclined surface, towards the other end.

7 Claims, 10 Drawing Sheets

(51) Int. Cl.
 *B65G 17/32* (2006.01)
 *B65G 47/14* (2006.01)
 *G01N 35/04* (2006.01)

(52) U.S. Cl.
 CPC ........... *G01N 2035/0406* (2013.01); *G01N 2035/0444* (2013.01)

(58) Field of Classification Search
 USPC ............................................ 198/396, 397.01
 See application file for complete search history.

(56) References Cited

U.S. PATENT DOCUMENTS

| | | | | |
|---|---|---|---|---|
| 3,724,656 A | * | 4/1973 | Sterling | B65G 47/1471 198/397.01 |
| 5,048,574 A | | 9/1991 | Rossie et al. | |
| 5,394,972 A | * | 3/1995 | Aidlin | B65G 47/1471 198/393 |
| 6,135,263 A | * | 10/2000 | Williams | B65G 47/1471 198/396 |
| 6,491,152 B1 | * | 12/2002 | Evers, Jr. | B65G 47/1471 198/393 |
| 7,597,189 B2 | * | 10/2009 | Hinsley | B65G 47/24 198/688.1 |
| 7,905,341 B1 | * | 3/2011 | Veno | B65G 47/1471 198/383 |
| 8,172,070 B2 | * | 5/2012 | Gassner | B65G 47/1471 198/396 |
| 8,646,591 B2 | * | 2/2014 | De Ruijter | A61J 3/007 198/397.01 |
| 2002/0106305 A1 | | 8/2002 | Willenbring et al. | |
| 2007/0269342 A1 | | 11/2007 | Kitagawa | |

FOREIGN PATENT DOCUMENTS

| | | |
|---|---|---|
| JP | 2004538222 A | 12/2004 |
| JP | 2007309792 A | 11/2007 |
| JP | 2011136802 A | 7/2011 |

\* cited by examiner

CONTAINER SUPPLY UNIT AND AUTOMATED ANALYZER

CROSS-REFERENCE TO RELATED APPLICATIONS

This application is the United States national phase of International Application No. PCT/JP2015/063236 filed May 7, 2015, and claims priority to Japanese Patent Application No. 2014-100075 filed May 14, 2014, the disclosures of which are hereby incorporated in their entirety by reference.

TECHNICAL FIELD

The present invention relates to container supply units that supply containers used for analyzing samples and automated analyzers that includes container supply units.

BACKGROUND ART

There have been known automated analyzers that perform quantitative measurement of specific substances contained in samples that are biological samples such as blood and urine. Disposable cuvettes (disposable reaction containers) that contain samples and reagents are used in the automated analyzers. Such automated analyzers include, for example, a reaction unit in which the cuvettes are arranged, a dispenser that dispenses the sample and the reagent into the cuvettes arranged in the reaction unit, and a container supply unit that supplies empty cuvettes to the reaction unit.

PTL 1 describes a technique relating to a sample analyzer that includes storage parts in which containers (cuvettes) for preparing a sample are stored. The sample analyzer described in PTL 1 includes a first storage part to which the cuvettes are introduced and a cuvette ejection part that ejects the cuvettes from the first storage part. This sample analyzer further includes a second storage part in which the cuvettes ejected by the cuvette ejection part are stored and a cuvettes taking part that takes out the cuvettes one cuvette after another from the second storage part.

The cuvette ejection part includes a circular belt that includes a plurality of holding plates, a chain to which the circular belt is attached, a sprocket with which the chain is engaged, a drive motor that drives the sprocket, and a housing cover that houses the circular belt.

CITATION LIST

Patent Literature

PTL 1: Japanese Unexamined Patent Application Publication No. 2007-309792

SUMMARY OF INVENTION

Technical Problem

With the sample analyzer described in PTL 1, portions of the plurality of holding plates where the cuvettes are placed have a rectangular plate shape. This increases versatility in orientation of the cuvettes placed on the holding plates. That is, there is a possibility of the cuvettes being placed on the holding plates in a variety of orientations. This causes the orientations of the cuvettes ejected from the cuvette ejection part to the second storage part to be unstable, and accordingly, there is a problem in that jamming of the cuvettes easily occurs in the cuvette taking part that takes out the cuvettes one cuvette after another from the second storage part.

An object of the present invention is, in consideration of the above-described problem, to provide a container supply unit and an automated analyzer that includes the container supply unit that can suppress in advance anomalous orientations of containers ejected from a container (cuvette) ejection part.

Solution to Problem

In order to address the above-described problem and achieve the object of the present invention, a container supply unit according to the present invention includes a container storage part in which a plurality of containers are stored, a container ejection part which ejects the plurality of containers stored in the container storage part, and a container alignment part which aligns the containers ejected from the container ejection part. The container ejection part includes a circular belt, a placement member, and a belt rotation mechanism. The placement member is provided on the circular belt and on which the containers are placed. The belt rotation mechanism rotates the circular belt in one direction and forms an outward leg along which the placement member moves upwards and a return leg along which the placement member moves downwards.

The placement member carries the containers placed thereon on the outward leg and ejects the containers between the outward leg and the return leg to the container alignment part. An upper portion of the placement member, the upper portion located on an upper side on the outward leg, includes a first inclined surface and a second inclined surface. The first inclined surface has one end provided on a circular belt side and another end separated from the circular belt, and the first inclined surface is inclined upwards on the outward leg towards the other end. The second inclined surface has one end continuous with the first inclined surface and another end separated from the circular belt, and the second inclined surface is inclined downwards on the outward leg towards the other end.

An automated analyzer according to the present invention includes a reaction unit which holds containers into which a sample and a reagent are dispensed and the above-described container supply unit which supplies the containers to the reaction unit.

The container supply unit and the automated analyzer having the above-described structures include the upper portion of the placement member, the upper portion located on the upper side on the outward leg, which includes the first inclined surface. The first inclined surface is inclined upwards on the outward leg towards the other end separated from the circular belt. Accordingly, an angle formed between the first inclined surface of the placement member and an outer circumferential surface of the circular belt is smaller than 90 degrees. Thus, the containers placed on the first inclined surface of the placement member are brought into contact with the outer circumferential surface of the circular belt, thereby the containers can be stably held by the placement member and the circular belt.

Furthermore, the containers having been moved onto the second inclined surface of the placement member slide down along the second inclined surface, and accordingly, are not placed on the placement member. This can prevent the occurrence of a situation in which the containers in an unstable orientation are placed on the placement member. As a result, the occurrence of a situation in which the containers ejected from the container ejection part are in anomalous orientations can be suppressed.

Also, in order to address the above-described problem and achieve the object of the present invention, a container supply unit according to the present invention includes a container storage part in which a plurality of containers are stored, a container ejection part which ejects the plurality of containers stored in the container storage part, and a container alignment part which aligns the containers ejected from the container ejection part. The container ejection part includes a circular belt, a placement member, and a belt rotation mechanism. The placement member is provided on the circular belt, and the containers are placed on the placement member. The belt rotation mechanism rotates the circular belt in one direction and forms an outward leg along which the placement member moves upwards and a return leg along which the placement member moves downwards.

The placement member carries the containers placed thereon on the outward leg and ejects the containers between the outward leg and the return leg to the container alignment part. The placement member includes a projection in a lower portion thereof, the lower portion located on a lower side on the outward leg. The projection is displaced relative to the circular belt between the outward leg and the return leg so as to flick the container placed on another container placed on an upper portion of a placement member positioned immediately downstream.

An automated analyzer according to the present invention includes a reaction unit which holds containers into which a sample and a reagent are dispensed and the above-described container supply unit which supplies the containers to the reaction unit.

In the container supply unit and the automated analyzer having the above-described structures, the lower portion of the placement member, the lower portion located on the lower side on the outward leg, is displaced relative to the circular belt between the outward leg and the return leg. The projection provided in the lower portion of the placement member flicks the container placed on the other container placed on the upper portion of the placement member. This can prevent the occurrence of a situation in which the containers in a state in which one of the containers is placed on another of the containers placed on the placement member, that is, the containers in a state in which two containers stacked one on top of the other, are ejected from the container ejection part. As a result, the occurrence of a situation in which the containers ejected from the container ejection part assume anomalous orientations can be suppressed.

Advantageous Effects of Invention

With the container supply unit and the automated analyzer according to the present invention, anomalous orientations of the containers ejected from the container ejection part can be suppressed in advance.

DESCRIPTION OF EMBODIMENTS

Figure 1:
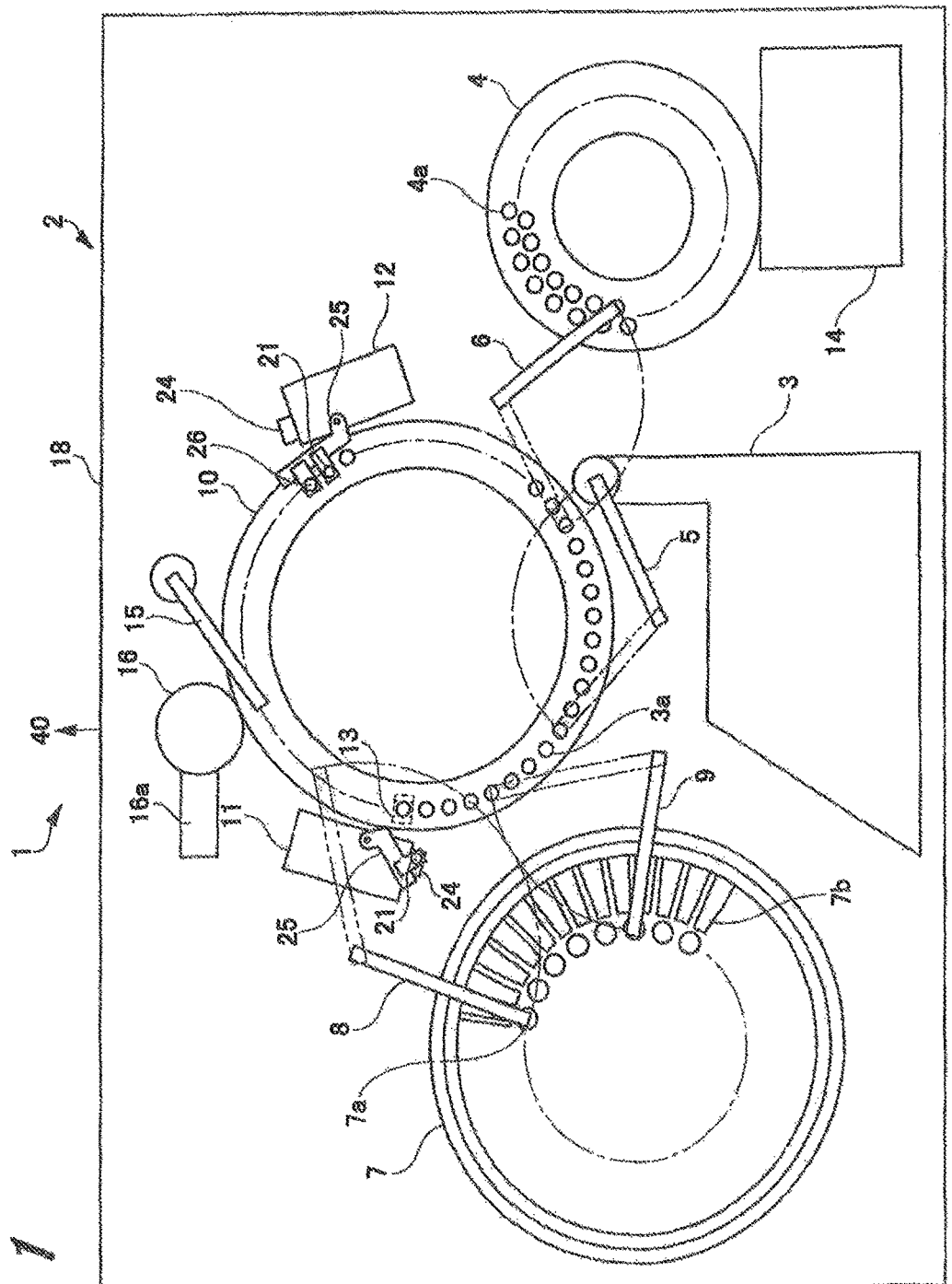
FIG. 1 is an outline structural view of an automated analyzer according to an embodiment of the present invention.

An example of an embodiment of a container supply unit and an automated analyzer according to the present invention will be described below with reference to FIGS. 1 to 10. In the drawings, the same reference numerals are used for similar parts. It should be understood that, although description will be written in the following order, the present invention is not necessarily limited to the following forms.

1-1. A structure of the Automated Analyzer
1-2. A Structure of Containers
1-3. A structure of the Container Supply Unit
1-4. Effects of the Container Supply Units
1-1. A Structure of the Automated Analyzer First, the automated analyzer according to an embodiment of the present invention is described with reference to FIG. 1.

FIG. 1 is an outline structural view of the automated analyzer according to the embodiment of the present invention.

[An Outline of the Automated Analyzer]

An immunoanalyzer that analyzes immunity such as an antigen-antibody reaction of a test sample is applied to the automated analyzer 1 of FIG. 1. An automated analyzer 1 includes a measurement device 2 and a controller 40. The controller 40 controls the entirety of the automated analyzer 1 including the measurement device 2 and analyzes measurement data output from the measurement device 2.

The automated analyzer 1 to which the immunoanalyzer is applied performs sensitive measurement using, for example, chemiluminescent enzyme immunoassay (CLEIA). The CLEIA mainly includes the following steps: a reaction step in which a sample (antigen or antibody) is caused to react with a reagent; a separation step (BF separation) in which a reaction product (bound) and unreacted substances (free) in a reaction container are separated from one another; and a measuring step in which the amount of light emitted by an immune complex generated by a reaction between the reagent and the sample is measured.

[A Measurement System of the Automated Analyzer]

Roughly classified, the measurement device 2 includes a container supply unit 3, a sample holding unit 4, a container carrying unit 5, a sample dispensing unit 6, a reagent thermal-insulation unit 7, a first reagent dispensing unit 8, a second reagent dispensing unit 9, an immunoenzyme reaction unit 10, a first BF separation unit 11, a second BF separation unit 12, a substrate-solution thermal-insulation storage 14, a container transfer unit 15, and a light emission measurement unit 16. Units including the container supply unit 3, the sample holding unit 4, and so forth, the substrate-solution thermal-insulation storage 14, the container transfer unit 15, and the light emission measurement unit 16 are housed in a device exterior body 18.

The container supply unit 3 contains a plurality of containers (cuvettes) 100 and disposes the plurality of containers 100 to a transfer position one by one. Each of the containers 100 having been disposed at the transfer position is carried by the container carrying unit 5 to the immunoenzyme reaction unit 10. The sample and the specified reagent are injected into the container 100 having been carried to the immunoenzyme reaction unit 10.

The container carrying unit 5 includes an arm and a holding portion. The container carrying unit 5 is movable upwards and downwards in the vertical direction and rotatable about a central axis defined by a vertical line passing through a proximal end portion of the container carrying unit 5. The holding portion is provided at a distal end portion of the arm. The container carrying unit 5 holds the container 100 disposed at the transfer position of the container supply unit 3 by using the holding portion and pivots the arm so as to carry the container 100 to a specified position of the immunoenzyme reaction unit 10 at specified timing.

The sample holding unit 4 includes a substantially cylindrical container-shaped turn table that is open at one end in the axial direction. A plurality of sample containers 4a are contained in the sample holding unit 4. The sample that include, for example, blood or urine collected from subjects is contained in the sample containers 4a. The plurality of sample containers 4a are spaced by a specified gap from one another in the circumferential direction of the sample holding unit 4. The sample holding unit 4 is rotatably supported by a drive mechanism (not illustrated) in the circumferential direction. The drive mechanism (not illustrated) rotates the sample holding unit 4 at a specified speed by a specified angle range at a time in the circumferential direction. In the example of FIG. 1, two rows of the sample containers 4a arranged in the circumferential direction of the sample holding unit 4 are spaced from each other by a specified gap in the radial direction of the sample holding unit 4. The samples may be diluted with a specified diluent.

The sample dispensing unit 6 includes a probe and an arm. The probe that sucks and discharges the sample is attached at a distal end of the sample dispensing unit 6. The sample dispensing unit 6 is movable upwards and downwards in the vertical direction and rotatable about a central axis defined by a vertical line passing through a proximal end portion of the sample dispensing unit 6. The sample dispensing unit 6 sucks with the probe the sample from each of the sample containers 4a having been moved to a specified position of the sample holding unit 4, pivots the arm, and, at specified timing, dispenses the sample into the container 100 at the specified position of the immunoenzyme reaction unit 10.

Similarly to the sample holding unit 4, the reagent thermal-insulation unit 7 includes a substantially cylindrical container-shaped turn table that is open at one end in the axial direction. The reagent thermal-insulation unit 7 is supported such that the reagent thermal-insulation unit 7 is rotatable in the circumferential direction by a drive mechanism (not illustrated). The drive mechanism (not illustrated) rotates in both forward and reverse directions the reagent thermal-insulation unit 7 at a specified speed by a specified angle range at a time in the circumferential direction.

The reagent thermal-insulation unit 7 contains first reagent containers 7a and second reagent containers 7b. The first reagent containers 7a are spaced by a specified gap from one another in the circumferential direction of the reagent thermal-insulation unit 7. The second reagent containers 7b are spaced by a specified gap from one another in the circumferential direction of the reagent thermal-insulation unit 7. As a first reagent, a magnetic reagent containing magnetic particles is contained in the first reagent containers 7a. These magnetic particles contained in the magnetic reagent react a target antigen in the sample. As a second reagent, a labeling reagent (enzyme antibody) is contained in the second reagent containers 7b. This labeling reagent reacts a reaction product produced by combining the antigen in the sample and the magnetic reagent with each other. A thermal insulation mechanism (not illustrated) maintains the temperature inside the reagent thermal-insulation unit 7 at a specified temperature. Thus, the first reagent (magnetic reagent) contained in the first reagent containers 7a and the second reagent (labeling reagent) contained in the second reagent containers 7b are thermally insulated and kept at the specified temperature.

The first reagent dispensing unit 8 includes a probe and an arm. The probe that sucks and discharges the sample is attached at a distal end of the first reagent dispensing unit 8. The first reagent dispensing unit 8 is movable upwards and downwards in the vertical direction and rotatable about a central axis defined by a vertical line passing through a proximal end portion of the first reagent dispensing unit 8. The first reagent dispensing unit 8 sucks with the probe the first reagent (magnetic reagent) from each of the first reagent containers 7a having been moved to a specified position of the reagent thermal-insulation unit 7, pivots the arm, and, at specified timing, dispenses the first reagent into the container 100 at a specified position of the immunoenzyme reaction unit 10.

The second reagent dispensing unit 9 has a similar structure to that of the first reagent dispensing unit 8. The second reagent dispensing unit 9 sucks with a probe the second reagent (labeling reagent) from each of the second reagent containers 7b having been moved to a specified position of the reagent thermal-insulation unit 7, pivots an arm, and, at specified timing, dispenses the second reagent into the container 100 at a specified position of the immunoenzyme reaction unit 10.

In the immunoenzyme reaction unit 10, an immunoreaction is performed between the sample in each of the containers 100 arranged in the circumferential direction and the specified reagent corresponding to an analysis item, and an enzyme reaction is performed between a chemiluminescent substrate and an immunocomplex generated in this immunoreaction. Similarly to the sample holding unit 4, the immunoenzyme reaction unit 10 includes a substantially cylindrical container-shaped turn table that is open at one end in the axial direction. The immunoenzyme reaction unit 10 is supported such that the immunoenzyme reaction unit 10 is rotatable in the circumferential direction by a drive mechanism (not illustrated). The drive mechanism (not illustrated) rotates the immunoenzyme reaction unit 10 at a specified speed by a specified angle range at a time in the circumferential direction. Here, the immunoenzyme reaction unit 10 is rotated counterclockwise. In the example of FIG. 1, the containers 100 arranged in a single row in the circumferential direction of the immunoenzyme reaction unit 10 are spaced by a specified gap in the radial direction of the immunoenzyme reaction unit 10. However, a row of the containers 100 for the first reagent and a row of the containers 100 for the second reagent which will be described later may be spaced from each other by a specified gap in the radial direction.

When the magnetic reagent is dispensed by the first reagent dispensing unit 8 into one of the container 100 into which the sample has been injected, the immunoenzyme reaction unit 10 agitates a mixture of the magnetic reagent and the sample using an agitating mechanism (not illustrated) so as to cause a immunoreaction to occur between the antigen in the sample and the magnetic reagent for a certain period of time (first immunoreaction). Next, the immunoenzyme reaction unit 10 moves this container 100 to a first magnetic collection mechanism (magnet 13) so as to magnetically collect by a magnetic force a reaction product which is a combination of the antigen and the magnetic reagent. Then, in this state, the inside of the container 100 is cleaned and unreacted substances that have not been reacted with the magnetic reagent are removed (first BF separation).

The first magnetic collection mechanism is secured at a position corresponding to the first BF separation unit 11 disposed near an outer peripheral portion of the immunoenzyme reaction unit 10. The turn table of the immunoenzyme reaction unit 10 includes two layers, that is a fixed lower layer and a rotatable upper layer. The magnet 13 as the first magnetic collection mechanism is disposed on the lower turn table. The container 100 is disposed on the upper turn table. The magnet 13 magnetically collects the reaction product in the container 100.

The first BF separation unit 11 includes an arm 25, a nozzle 21, and a cleaning bath 24. The nozzle 21 is attached to the arm 25. The arm 25 is movable upwards and downwards in the vertical direction and rotatable about a central axis defined by a vertical line passing through a proximal end portion of the arm 25. This arm 25 moves the nozzle 21 to the container 100 existing at a first BF separation position of the immunoenzyme reaction unit 10 and to the cleaning bath 24 existing at a nozzle cleaning position on the first BF separation unit 11 side. At the first BF separation position, the nozzle 21 discharges and sucks a cleaning solution into and from the container 100 so as to clean the container 100 into which the sample and the magnetic reagent have been injected, thereby removing the unreacted substances that have not been reacted with the magnetic reagent (BF cleaning).

The first BF separation unit 11 performs the first BF separation when the container 100 is carried to the first BF separation position. Through the first BF separation and the BF cleaning, the reaction product which is the combination of the target antigen in the sample and the magnetic reagent is magnetically collected in the container 100. When the first BF separation is completed, the arm 25 moves the nozzle 21 to the nozzle cleaning position where the cleaning bath 24 exists.

After the first BF separation, when the labeling reagent is dispensed by the second reagent dispensing unit 9 into the container 100 where the reaction product remains, the immunoenzyme reaction unit 10 agitates the mixture of the magnetic reagent and the sample using an agitating mechanism (not illustrated) so as to cause a immunoreaction to occur between the reaction product and the labeling reagent for a certain period of time (second immunoreaction). Next, the immunoenzyme reaction unit 10 moves this container 100 to a second magnetic collection mechanism (not illustrated) so as to magnetically collect by a magnetic force an immunocomplex which is a combination of the reaction product and the labeling reagent. Then, in this state, the inside of the container 100 is cleaned and unreacted substances that have not been reacted with the labeling reagent are removed (second BF separation).

The second magnetic collection mechanism includes a magnet similar to the magnet 13 of the first magnetic collection mechanism. The second magnetic collection mechanism is secured at a position corresponding to the second BF separation unit 12 disposed near the outer peripheral portion of the immunoenzyme reaction unit 10. In the example of FIG. 1, the magnet included in the second magnetic collection mechanism is disposed below a nozzle 21 where a second BF separation position exists.

The second BF separation unit 12 has a similar structure to that of the first BF separation unit 11 and is spaced from the first BF separation unit 11 by a specified distance in the circumferential direction. An arm 25 is movable upwards and downwards in the vertical direction and rotatable about a central axis defined by a vertical line passing through a proximal end portion of the arm 25. This arm 25 moves the nozzle 21 to the container 100 existing at a second BF separation position of the immunoenzyme reaction unit 10 and to a cleaning bath 24 existing at a nozzle cleaning position on the second BF separation unit 12 side. At the second BF separation position, the nozzle 21 discharges and sucks a cleaning solution into and from the container 100 so as to clean the container 100 into which the labeling reagent has been injected, thereby removing excessive unreacted substances that have not been reacted with the labeling reagent (BF cleaning).

The second BF separation unit 12 performs the second BF separation when the container 100 is carried to the second BF separation position. Through the second BF separation and the BF cleaning, the immunocomplex which is a combination of the labeling reagent and the reaction product formed of the target antigen in the sample and the magnetic reagent is magnetically collected in the container 100. When the second BF separation is completed, the arm 25 moves the nozzle 21 to a nozzle cleaning position where the cleaning bath 24 exists.

Furthermore, a substrate solution dispensing unit 26 is attached to the arm 25 of the second BF separation unit 12. The substrate solution dispensing unit 26 is disposed at a position further from a rotating shaft of the arm 25 than the nozzle 21. The substrate solution dispensing unit 26 is connected through a tube (not illustrated) to the substrate-solution thermal-insulation storage 14 that contains the substrate solution so as to thermally insulate the substrate solution. The substrate solution dispensing unit 26 dispenses into the container 100 after the second BF separation the substrate solution containing the chemiluminescent substrate that specifically reacts with the labeling reagent for the immunocomplex which is the combination of the magnetic reagent, the antigen, and the labeling reagent (enzyme antibody). The container 100 into which the substrate solution has been injected is carried to a specified position through the rotation of the immunoenzyme reaction unit 10. The container 100 having been carried to the specified position is transferred to the light emission measurement unit 16 by the container transfer arm 15.

The light emission measurement unit 16 is a measurement unit including a photomultiplier tube (PMT) 16a as a detector and measures through photocounting a light emitting phenomenon caused by the immunocomplex and the chemiluminescent substrate. That is, the light emission measurement unit 16 measures the amount of light emission. A light measurement signal corresponding to a luminous flux (amount of light emission) detected by the light emission measurement unit 16 is digitized by an analog to digital converter (not illustrated). The digitized light measurement signal is input to a controller 40 through a serial interface or the like (not illustrated) so as to be subjected to an analytical process.

1-2. A Structure of the Containers

Next, a structure of the containers 100 is described with reference to FIG. 2.

Figure 2:
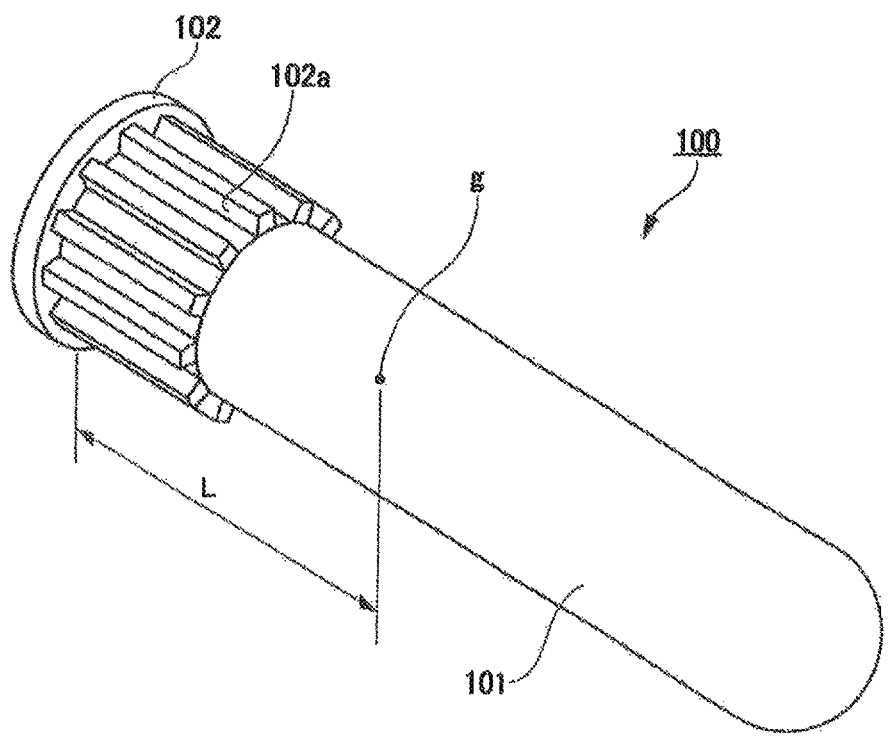
FIG. 2 is a perspective view illustrating a container used in the automated analyzer according to the embodiment of the present invention.

FIG. 2 is a perspective view illustrating one of the containers 100 used in the automated analyzer 1.

As illustrated in FIG. 2, the container 100 has a bottomed cylindrical shape and includes a body portion 101 and a neck portion 102. Examples of the material of the container 100 include resin and glass. The container 100 is transparent or semitransparent.

One end portion of the body portion 101 in the axial direction forms a bottom portion of the container 100 and has a substantially semispherical shape. The neck portion 102 is provided at the other end portion of the body portion 101 in the axial direction. An outer diameter of the neck portion 102 is larger than an outer diameter of the body portion 101. Accordingly, a step is formed between the neck portion 102 and the body portion 101. Grooves 102a extending in the axial direction of the neck portion 102 are formed in an outer circumferential surface of the neck portion 102.

It is sufficient that the neck portion of the container have a lager outer diameter than the outer diameter of the body portion. The neck portion does not necessarily have the grooves. The neck portion of the container may have, for example, a first outer diameter portion that is larger than the outer diameter of the body portion and a second outer diameter portion that is larger than the outer diameter of the first outer diameter portion, or the outer diameter of part of the neck portion may have a larger outer diameter than the outer diameter of the body portion.

A center of gravity g of the container 100 exists at a position displaced slightly close to the neck portion 102 side from a central portion of the container 100 in the axial direction. According to the present embodiment, in the axial direction of the body portion 101, the distance between one end of the container 100 on the neck portion 102 side and the center of gravity g is defined as a center of gravity distance L. That is, out of the distances between the center of gravity g and both the ends of the container 100 in the axial direction, the shorter distance is the center of gravity distance L.

1-3. A Structure of the Container Supply Unit

Next, a detailed structure of the container supply unit 3 is described with reference to FIGS. 3 to 7.

Figure 3:
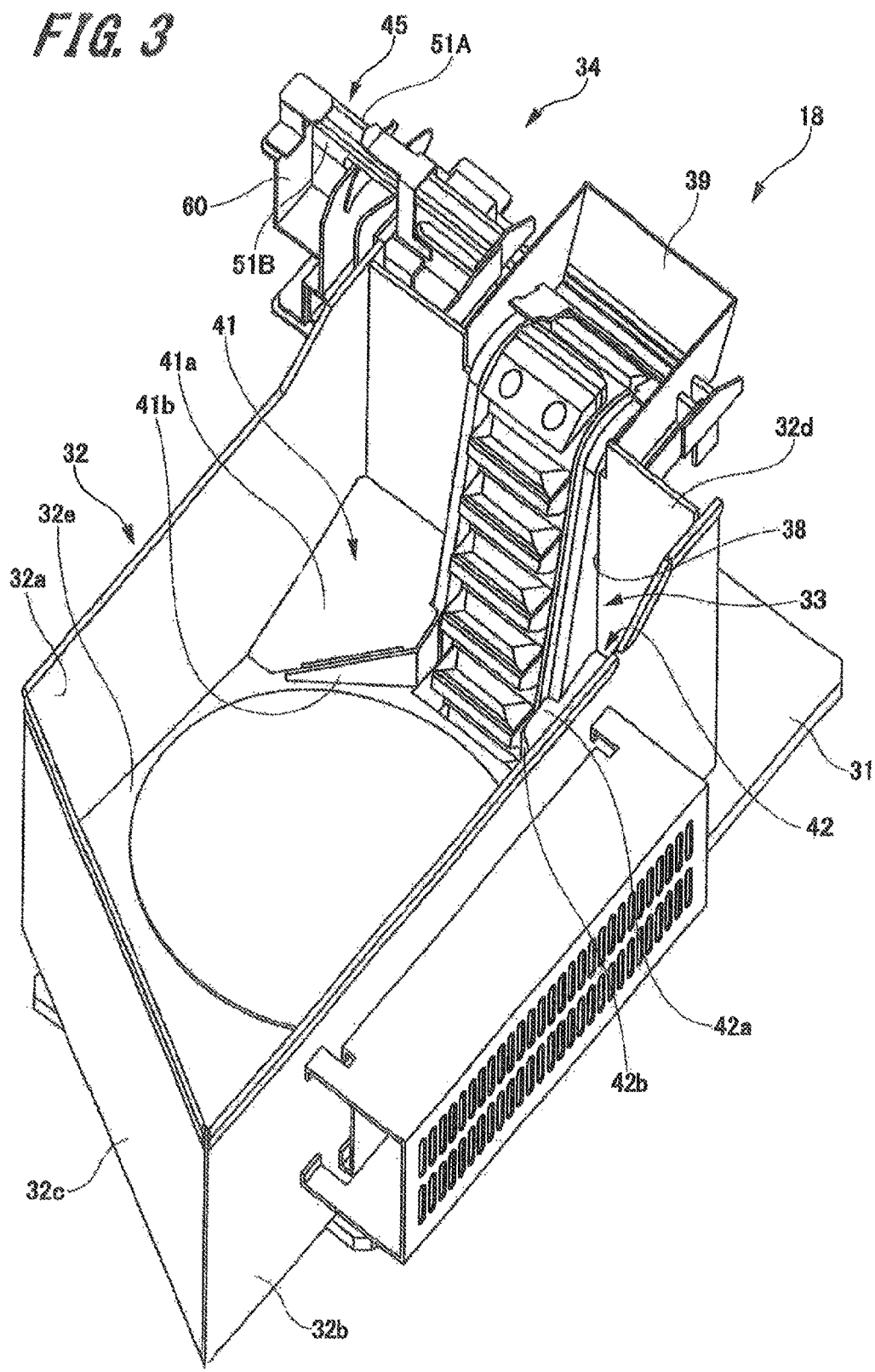
FIG. 3 is a perspective view (No. 1) of a container supply unit according to the embodiment of the present invention.
Figure 4:
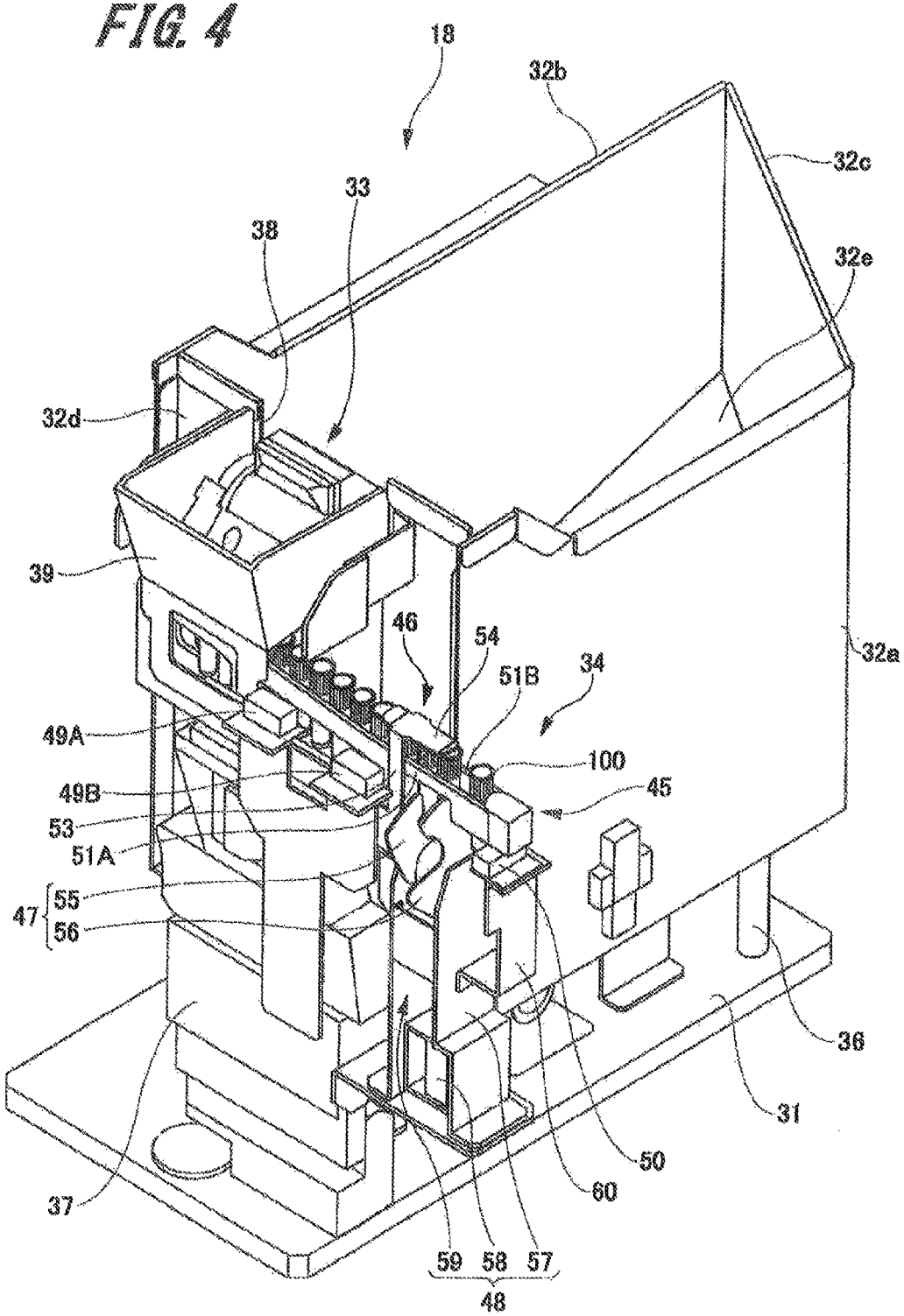
FIG. 4 is a perspective view (No. 2) of the container supply unit according to the embodiment of the present invention.

FIGS. 3 and 4 are perspective views of the container supply unit 3.

As illustrated in FIGS. 3 and 4, the container supply unit 3 includes a base part 31, a container storage part 32, a container ejection part 33, and a container alignment part 34. The base part 31 has a rectangular shape having an appropriate thickness.

[The Container Storage Part]

The container storage part 32 is supported by a plurality of storage part support members 36 provided on the base part 31 (see FIG. 4). The container storage part 32 has a hollow box shape that is open at the top. The plurality of containers 100 are stored in the container storage part 32 (see FIG. 2). This container storage part 32 includes four side plates 32a, 32b, 32c, and 32d and a bottom plate 32e. The side plates 32a and 32b face each other, and the side plates 32c and 32d face each other.

The side plate 32d has a cut 38 extending in the up-down direction. The container ejection part 33 is disposed in this cut 38. Furthermore, a cover member 39 that covers the cut 38 and the container ejection part 33 is attached to the side plate 32d. One end portion of an alignment rail structure 45 of the container alignment part 34 is disposed in the cover member 39. The alignment rail structure 45 will be described later.

An inner surface of the bottom plate 32e is inclined downwards from the side plate 32c towards the side plate 32d. With this structure, the plurality of containers 100 stored in the container storage part 32 are guided by the bottom plate 32e so as to move towards the side plate 32d side where the container ejection part 33 is disposed. Furthermore, container guide auxiliary members 41 and 42 are provided on the inner surface of the bottom plate 32e. These container guide auxiliary members 41 and 42 are disposed on both sides of the container ejection part 33.

The container guide auxiliary members 41 and 42 include respective first guide surfaces 41a and 42a and respective second guide surfaces 41b and 42b. The first guide surfaces 41a and 42a face an opening of the container ejection part 33 and guide the containers 100 positioned beside the container ejection part 33 in the container storage part 32 towards the substantially center of the container storage part 32. The second guide surfaces 41b and 42b are flat surfaces parallel to the up-down direction and guide the containers 100 being guided by the inner surface of the bottom plate 32e so as to move towards the side plate 32d side towards the container ejection part 33.

The opening of the container storage part 32 is closed by a lid for a storage part (not illustrated) provided in the device exterior body 18 (see FIG. 1). In order to introduce the plurality of containers 100 to the container storage part 32, the lid for a storage part is opened, so that the opening of the container storage part 32 is exposed.

The container ejection part 33 ejects the plurality of containers stored in the container storage part 32 to the outside of the side plate 32d. The structure of the container ejection part 33 will be described later with reference to FIGS. 6 to 8.

[The Container Alignment Part]

Next, the container alignment part 34 is described with reference to FIGS. 3 to 5.

Figure 5:
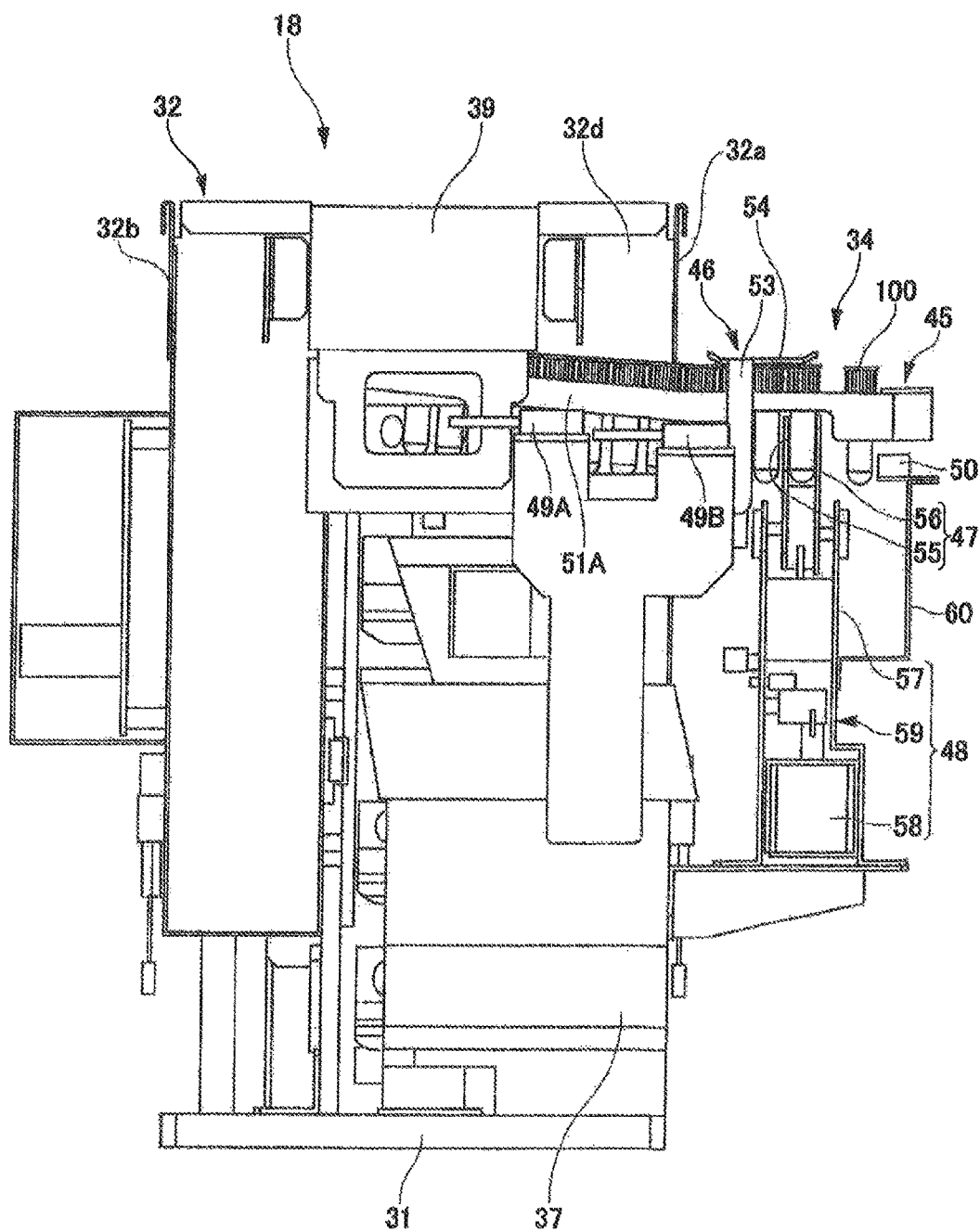
FIG. 5 is a side view of the container supply unit according to the embodiment of the present invention.

FIG. 5 is a side view of the container supply unit 3.

As illustrated in FIGS. 3 to 5, the container alignment part 34 is supported by a plurality of alignment part support members 37 provided on the base part 31 (see FIG. 4). The container alignment part 34 aligns the containers 100 ejected from the container ejection part 33.

The container alignment part 34 includes the alignment rail structure 45, an orientation adjustment member 46, a shutter member 47, a shutter drive mechanism 48, number monitoring sensors 49A and 49B, a container presence/absence sensor 50, and a vibration generator (not illustrated). The vibration generator vibrates the alignment rail structure.

The alignment rail structure 45 includes two flat plates 51A and 51B that face each other. These flat plates 51A and 51B each have a laterally elongated substantially rectangular shape and are disposed substantially parallel to the side plate 32d. The distance between flat surfaces of the flat plates 51A and 51B facing each other is larger than the outer diameter of the body portion 101 of each of the containers 100 and smaller than the outer diameter of the neck portion 102 of each of the containers 100.

The one end portion of the alignment rail structure 45 in the longitudinal direction is inserted through the above-described cover member 39 so as to be disposed inside the cover member 39. That is, each of the containers 100 ejected from the container ejection part 33 is passed to the alignment rail structure 45 in the cover member 39. Furthermore, the alignment rail structure 45 is slightly inclined such that the level of the one end portion is higher than the level of the other end portion in the longitudinal direction.

When the container 100 is ejected to a space between the two flat plates 51A and 51B of the alignment rail structure 45, the body portion 101 passes through the space between the flat plates 51A and 51B and the neck portion 102 is brought into engagement with upper ends of the flat plates 51A and 51B. Thus, the container 100 ejected to the container alignment part 34 is held by the alignment rail structure 45 while being oriented such that the axial direction of the container 100 is parallel to the up-down direction and the bottom portion of the container 100 is positioned on the lower side.

The vibration generator (not illustrated) is attached to the alignment rail structure 45 or one of the alignment part support members 37 that supports the alignment rail structure 45. Examples of this vibration generator include, for example, a pneumatic vibrator, an electrical vibrator, a high-frequency vibrator, and so forth. Due to vibration of the alignment rail structure 45 caused by the vibration generator (not illustrated), the container 100 held by the alignment rail structure 45 gradually moves towards the other end portion of the alignment rail structure 45. The other end portion of the alignment rail structure 45 is set at the transfer position where the container 100 is passed to the above-described container carrying unit 5.

The container 100 held by the alignment rail structure 45 while being oriented such that the neck portion 102 is positioned on the lower side is, during a movement along the alignment rail structure 45, brought into contact with a side plate portion of the cover member 39 through which the alignment rail structure 45 is inserted. Thus, the container 100 rotates about a virtual line extending in a direction perpendicular to the two flat plates 51A and 51B of the alignment rail structure 45, so that the container 100 is held by the alignment rail structure 45 while being oriented such that the bottom portion is positioned on the lower side.

According to the present embodiment, the container 100 held by the alignment rail structure 45 while being oriented such that the neck portion 102 thereof is positioned on the lower side is brought into contact with the cover member 39. Alternatively, the container supply unit and the automated analyzer according to the present invention may include, independently of the cover member 39, an orientation correcting piece with which the container 100 being oriented such that the neck portion 102 is positioned on the lower side is brought into contact.

Furthermore, when the container 100 ejected from the container ejection part 33 does not pass through the space between the two flat plates 51A and 51B of the alignment rail structure 45 and moves out of the container alignment part 34 and, the cover member 39 guides the container 100 so that the container 100 is directed to the alignment rail structure 45 again.

As illustrated in FIGS. 4 and 5, the orientation adjustment member 46 is disposed between the cover member 39 and the transfer position of the alignment rail structure 45. The orientation adjustment member 46 includes an attachment piece 53 attached to the alignment part support member 37 and an adjustment piece 54 continuous with the attachment piece 53 and disposed above the alignment rail structure 45.

The adjustment piece 54 is a substantially rectangular plate member that includes a flat surface intersecting the up-down direction and that extends in the longitudinal direction of the alignment rail structure 45. The distance between a lower surface of the adjustment piece 54 and upper ends of the two flat plates 51A and 51B of the alignment rail structure 45 is slightly larger than the length of the neck portion 102 of the container 100 in the axial direction. Furthermore, both ends of the adjustment piece 54 in the longitudinal direction are inclined upwards.

When the length of each of the containers 100 projecting from the upper ends of the flat plates 51A and 51B is larger than the length of the neck portion 102 in the axial direction, the adjustment piece 54 is brought into engagement with the neck portion 102 of the container 100 so as to move the container 100 downwards. In this way, when the containers 100 have passed through the adjustment piece 54 of the orientation adjustment member 46, the lengths of the containers 100 projecting from the upper ends of the flat plates 51A and 51B are uniformly set to a length substantially equal to the length of the neck portion 102 in the axial direction.

The shutter member 47 is disposed at a position below the alignment rail structure 45 and between the orientation adjustment member 46 and the transfer position of the alignment rail structure 45. This shutter member 47 is rotatably supported by a shutter support portion 57 of the shutter drive mechanism 48 to be described later and rotates about a rotational axis extending substantially parallel to the longitudinal direction of the alignment rail structure 45.

The shutter member 47 includes a first shutter piece 55 and a second shutter piece 56. The first shutter piece 55 and the second shutter piece 56 are respectively formed of plates that each have a surface intersecting the longitudinal direction of the alignment rail structure 45 so as to interrupt a movement of the containers 100 along the alignment rail structure 45 for a specified period of time.

The first shutter piece 55 and the second shutter piece 56 are shifted from each other in the rotational direction of the shutter member 47. With this structure, when the first shutter piece 55 interrupts the movement of the containers 100 along the alignment rail structure 45, the second shutter piece 56 does not interrupt the movement of the containers 100. In contrast, when the second shutter piece 56 interrupts the movement of the containers 100 along the alignment rail structure 45, the first shutter piece 55 does not interrupt the movement of the containers 100.

Furthermore, the distance between the first shutter piece 55 and the second shutter piece 56 is slightly larger than the outer diameter of the body portion 101 of the containers 100. Thus, when the movement of the containers 100 is alternately interrupted by the first shutter piece 55 and the second shutter piece 56, the plurality of containers 100 held by the alignment rail structure are taken out one container after another so as to be disposed at the transfer position of the alignment rail structure.

The shutter drive mechanism 48 includes the shutter support portion 57, a solenoid 58, and a linkage 59. The shutter member 47 is rotatably supported by the shutter support portion 57. The solenoid 58 is secured to the shutter support portion 57. The linkage 59 transmits a drive force of the solenoid 58 to the shutter member 47 (shutter pieces 55, 56).

As the shutter drive mechanism that rotates the shutter member 47, any of a variety of mechanisms such as, for example, a belt mechanism that uses a circular belt and a pulley, a gear mechanism that uses a stepping motor and a gear train, and a chain mechanism that uses a sprocket and a chain can be applied.

Furthermore, the shutter drive mechanism 48 according to the present embodiment rotates the shutter member 47. Alternatively, the shutter drive mechanism of the container supply unit and the automated analyzer according to the present invention may linearly move the shutter member. Also in this case, the first shutter piece and the second shutter piece are provided, and the movement of the containers 100 is alternately interrupted by two shutter pieces.

Alternatively, the shutter member of the container supply unit and the automated analyzer according to the present invention may include the first shutter piece and the second shutter piece which are prepared independently of each other. In this case, the first shutter piece and the second shutter piece may be provided with respective drive mechanisms.

The number monitoring sensors 49A and 49B are disposed between the cover member 39 and the orientation adjustment member 46. These number monitoring sensors 49A and 49B are, for example, photosensors that detect whether or not the containers 100 exist at positions that faces the number monitoring sensors 49A and 49B.

When both the number monitoring sensors 49A and 49B detect that the containers 100 exists at the positions that face the number monitoring sensors 49A and 49B, it can be determined that the number of the containers 100 before passing through the orientation adjustment member 46 is equal to or more than a specified number (five according to the present embodiment). Thus, information that at least the specified number of the containers 100 are continuously supplied to a downstream process can be transmitted to a control unit that controls the downstream process.

When at least one of the number monitoring sensors 49A and 49B detects that there is no container 100 at the position that faces the at least one of the number monitoring sensors 49A and 49B, it can be determined that the number of the containers 100 before passing through the orientation adjustment member 46 is less than the specified number. Thus, information that there will not be a continuous supply of at least the specified number of the containers 100 to the downstream process can be transmitted to the control unit that controls the downstream process.

The container presence/absence sensor 50 is attached to a bracket 60 secured to the shutter support portion 57. The container presence/absence sensor 50 faces the container 100 disposed at the transfer position of the alignment rail structure 45. The container presence/absence sensor 50 is, for example, a photosensor that detects whether or not the container 100 exists at a position (transfer position) that faces the container presence/absence sensor 50.

[The Container Ejection Part]

Next, the structure and operation of the container ejection part 33 are described with reference to FIGS. 6 to 8.

Figure 6:
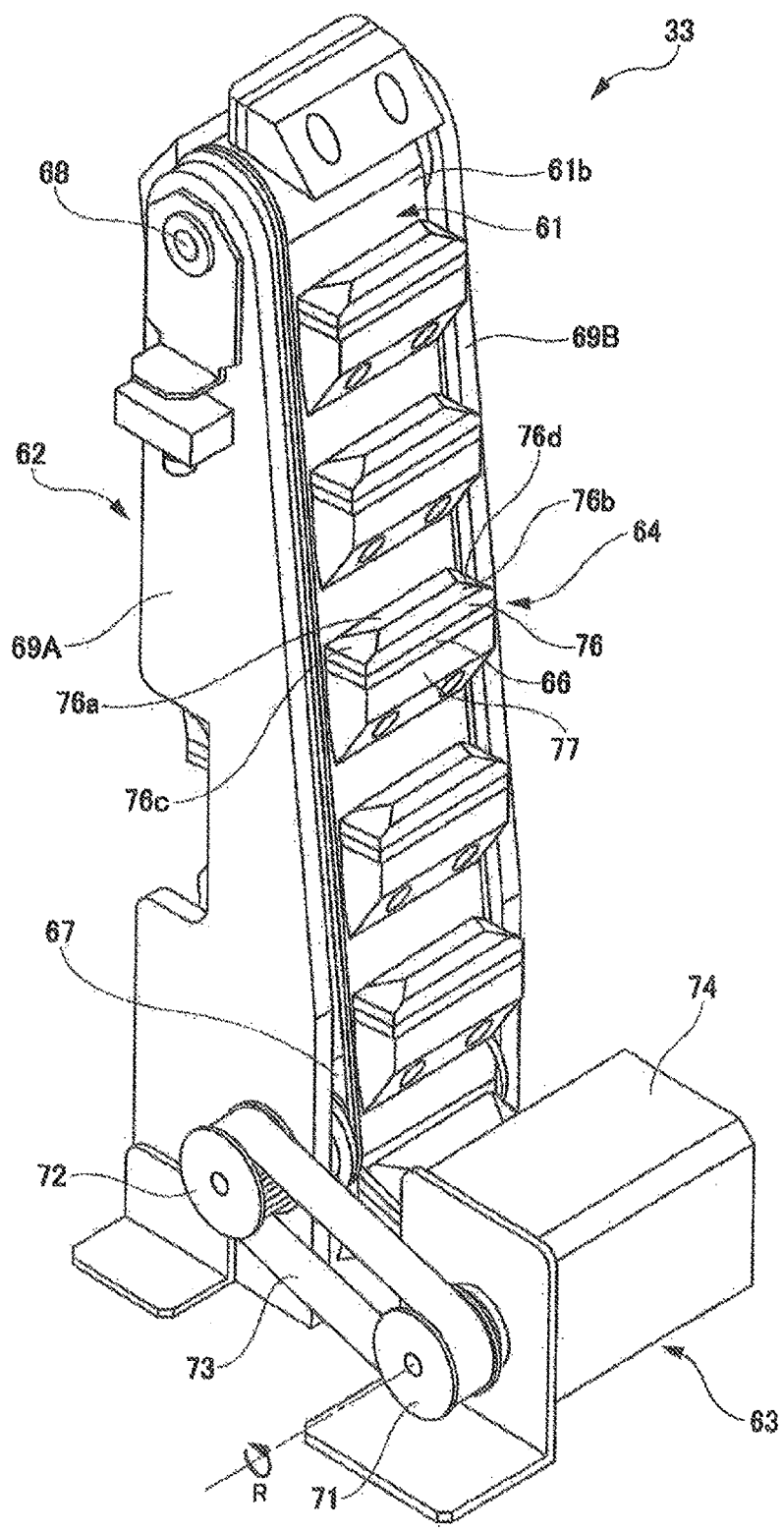
FIG. 6 is a perspective view of a container ejection part of the container supply unit according to the embodiment of the present invention.

FIG. 6 is a perspective view of the container ejection part 33. FIG. 7 is a perspective view of a circular belt of the container ejection part 33.

As illustrated in FIG. 6, the container ejection part 33 includes a circular belt 61, a belt support mechanism 62, a belt rotation mechanism 63, and placement members 64. The circular belt 61 is rotatably supported by the belt support mechanism 62. The belt rotation mechanism 63 rotates the circular belt 61. The placement members 64 are provided on the circular belt 61.

The circular belt 61 has an endless shape and looped over a drive roller 67 and a driven roller 68 of the belt support mechanism 62. The drive roller 67 and the driven roller 68 will be described later. Hereafter, a surface of the circular belt 61 in contact with the drive roller 67 and the driven roller 68 is referred to as an inner circumferential surface 61a and an opposite surface of the circular belt 61 to the inner circumferential surface 61a is referred to as an outer circumferential surface 61b (see FIG. 7). Examples of the material of the circular belt 61 include a rubber material, synthetic resin, metal wire, and so forth.

Figure 7:
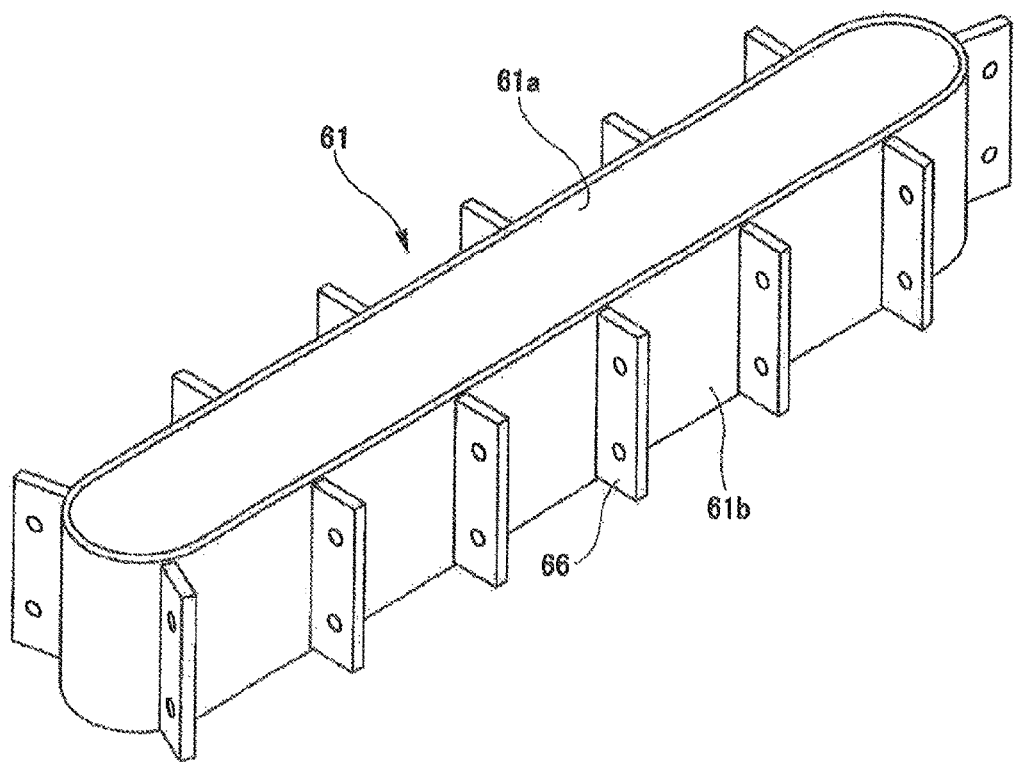
FIG. 7 is a perspective view of a circular belt of the container ejection part of the container supply unit according to the embodiment of the present invention.

As illustrated in FIG. 7, a plurality of holding plates 66 are provided on the outer circumferential surface 61b of the circular belt 61. The plurality of holding plates 66 are space from one another by a specified gap in the circumferential direction of the circular belt 61. The holding plates 66 each have a rectangular plate shape. The long side of the holding plate 66 extends in the width direction of the circular belt 61 and the short side of the holding plate 66 extends substantially perpendicularly to the circular belt 61. The plurality of holding plates 66 are parts of the placement members 64.

As illustrated in FIG. 6, the belt support mechanism 62 includes the drive roller 67, the driven roller 68, and a pair of roller support plates 69A and 69B. Each of the pair of roller support plates 69A and 69B is formed of a substantially rectangular plate body extending in the up-down direction. One of flat surfaces of the roller support plate 69A faces one of flat surfaces of the roller support plate 69B face.

The drive roller 67 is disposed between the pair of roller support plates 69A and 69B and rotatably supported at lower portions of the pair of roller support plates 69A and 69B. The driven roller 68 is disposed between the pair of roller support plates 69A and 69B and rotatably supported at upper portions of the pair of roller support plates 69A and 69B. With this structure, the circular belt 61 looped over the drive roller 67 and the driven roller 68 has a circular shape elongated in the up-down direction.

The belt rotation mechanism 63 is disposed below the bottom plate 32e (see FIG. 3) of the container storage part 32. That is, the belt rotation mechanism 63 is disposed outside the container storage part 32. The belt rotation mechanism 63 includes a drive pulley 71, a driven pulley 72, a timing belt 73, and a motor 74.

The motor 74 is, for example, a stepping motor, and the drive pulley 71 is secured to a rotating shaft of the motor 74. The driven pulley 72 is secured to a rotating shaft of the drive roller 67 inserted through the roller support plate 69A. The timing belt 73 is looped over the drive pulley 71 and the driven pulley 72.

The rotating shaft of the motor 74 normally rotates in an R direction of FIG. 6. This rotates the drive pulley 71 in the R direction, and a rotating force of the drive pulley 71 is transmitted to the driven pulley 72 through the timing belt 73. This rotates in the R direction the driven pulley 72 and the drive roller 67 to which the driven pulley 72 is secured, and accordingly, the circular belt 61 rotates in the R direction.

As a result, an outward leg along which the holding plates 66 (placement members 64) move upwards and a return leg along which the holding plates 66 (placement members 64) move downwards are formed in the circular belt 61. The outward leg of the circular belt 61 is disposed in the container storage part 32, and the return leg of the circular belt 61 is disposed outside the container storage part 32 (see FIG. 3).

The outward leg of the circular belt 61 is switched to the return leg through a curved portion which is an upper portion of the circular belt 61 (this curved portion is referred to as an "upper curved portion" hereafter). The return leg of the circular belt 61 is switched to the outward leg through a curved portion which is a lower portion of the circular belt 61 (this curved portion is referred to as a "lower curved portion" hereafter). The lower curved portion of the circular belt 61 together with the belt rotation mechanism 63 is disposed below the bottom plate 32e (see FIG. 3) of the container storage part 32.

Each of the placement members 64 includes the above-described holding plate 66, an upper formation piece 76, and a lower formation piece 77. The upper formation piece 76 is secured to one of flat surfaces of the holding plate 66. The lower formation piece 77 is secured to the other flat surface of the holding plate 66. Examples of the material of the upper formation piece 76 and the lower formation piece 77 include a rubber material, synthetic resin, and so forth. The upper formation piece 76 forms an upper portion of the placement member 64 on the outward leg of the circular belt 61. The lower formation piece 77 forms a lower portion of the placement member 64 on the outward leg of the circular belt 61.

The upper formation piece 76 is formed of a rectangular plate body having substantially the same planar shape as that of the holding plate 66. The upper formation piece 76 is removably secured to the holding plate 66 with screws. One of flat surfaces of the upper formation piece 76 is in contact with the one of the flat surfaces of the holding plate 66. The longitudinal direction of the upper formation piece 76 is substantially parallel to the width direction of the circular belt 61, and the width direction of the upper formation piece 76 is substantially perpendicular to the width direction of the circular belt 61.

A first inclined surface 76a, a second inclined surface 76b, a third inclined surface 76c, and a fourth inclined surface 76d are formed on a side of the upper formation piece 76 opposite to the one of the flat surfaces. The first inclined surface 76a and the second inclined surface 76b are adjacent to each other in the width direction of the upper formation piece 76. The first inclined surface 76a is provided on the circular belt 61 side.

On the outward leg of the circular belt 61, one end of the first inclined surface 76a faces the outer circumferential surface 61b of the circular belt 61. This first inclined surface 76a is inclined such that the height of the first inclined surface 76a gradually increases from the one end on the circular belt 61 side towards the other end separated from the circular belt 61. Also on the outward leg of the circular belt 61, the second inclined surface 76b is inclined such that the height of the second inclined surface 76b gradually reduces from one end continuous with the first inclined surface 76a towards the other end separated from the circular belt 61.

The third inclined surface 76c is formed at one end portion of the upper formation piece 76 in the longitudinal direction and adjacent to the first inclined surface 76a and the second inclined surface 76b. On the outward leg of the circular belt 61, the third inclined surface 76c is inclined such that the height of the third inclined surface 76c reduces towards the one end of the upper formation piece 76 in the longitudinal direction.

The fourth inclined surface 76d is formed at the other end portion of the upper formation piece 76 in the longitudinal direction and adjacent to the first inclined surface 76a and the second inclined surface 76b. On the outward leg of the circular belt 61, the fourth inclined surface 76d is inclined such that the height of the fourth inclined surface 76d reduces towards the other end of the upper formation piece 76 in the longitudinal direction.

Figure 8:
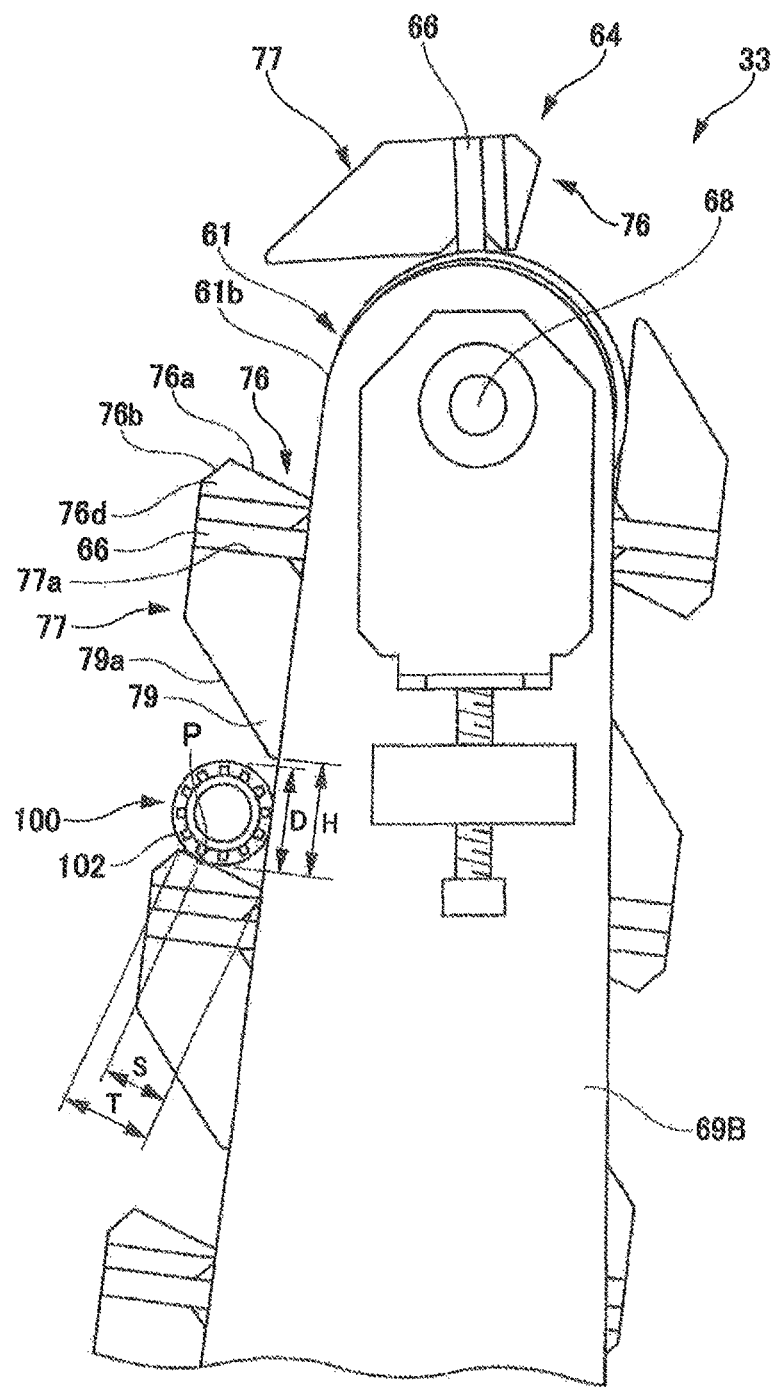
FIG. 8 is an explanatory view illustrating operation of the container ejection part of the container supply unit according to the embodiment of the present invention.

As illustrated in FIG. 8, the distance between the one end (a side facing the circular belt 61) of the first inclined surface 76a and the other end (a side serving as a border with the second inclined surface 76b) of the first inclined surface 76a is defined as a distance T. Also, a contact point where the neck portion 102 of the container 100 in contact with the outer circumferential surface 61b of the circular belt 61 is in contact with a virtual line that is perpendicular to the one end of the first inclined surface 76a and parallel to the first inclined surface 76a is defined as a contact point P. The distance T of the first inclined surface 76a is set to be larger than a contact point distance S that is a distance between the one end of the first inclined surface 76a and the contact point P.

Thus, when the axial direction of the container 100 placed on the upper formation piece 76 is substantially parallel to the width direction of the circular belt 61, the neck portion 102 of the container 100 is brought into contact with the outer circumferential surface 61b of the circular belt 61 and the first inclined surface 76a. As a result, the orientation of the container 100 in which the axial direction of the container 100 is substantially parallel to the width direction of the circular belt 61 can be stabilized, and accordingly, the container 100 can be prevented from dropping from the upper formation piece 76 (placement member 64) on the outward leg of the circular belt 61.

Furthermore, the contact point distance S is set to be smaller than the above-described center of gravity distance L (see FIG. 2). Thus, when the axial direction of the container 100 having moved onto the upper formation piece 76 is substantially perpendicular to the width direction of the circular belt 61, the container 100 drops from the upper formation piece 76 (placement member 64) on the outward leg of the circular belt 61. That is, the container 100 is not placed on the upper formation piece 76 in a state in which the axial direction of the container 100 is substantially perpendicular to the width direction of the circular belt 61.

Furthermore, the length of the one end of the first inclined surface 76a is set to be equal to or smaller than the length of the container 100 in the axial direction. Thus, when two containers 100 oriented such that the axial direction of these containers 100 is substantially parallel to the width direction of the circular belt 61 are placed on the upper formation piece 76, the center of gravity g of at least one of the two containers 100 is likely to exist outside the upper formation piece 76. This can reduce the likelihood of two containers 100 oriented such that the axial direction of these containers 100 is substantially parallel to the width direction of the circular belt 61 being placed on the upper formation piece 76.

According to the present embodiment, the center of gravity g of the container 100 exists at a position displaced slightly close to the neck portion 102 side from the central portion of the container 100 in the axial direction. Thus, when the length of the side of the first inclined surface 76a along the circular belt 61 is equal to the length of the container 100 in the axial direction, centers of gravity g of two containers 100 the neck portions 102 of which face each other may be positioned on the first inclined surface 76a. In such a case, the two containers 100 are placed on the first inclined surface 76a and carried upwards while projecting from both sides of the upper formation piece 76 in the longitudinal direction.

However, when the first inclined surface 76a (placement member 64) on which the two containers 100 are placed reaches the upper curved portion of the circular belt 61 and passes through the cut 38 provided in the side plate 32d, the two containers 100 are brought into contact with the side plate 32d. As a result, the two containers 100 are moved out of and drop from the upper formation piece 76 (placement member 64).

The length of the one end (the side along the circular belt 61) of the first inclined surface 76a according to the present invention may be equal to or smaller than twice the above-described center of gravity distance L. In this case, the center of gravity g of at least one of two containers 100 oriented such that the axial direction of these containers 100 is substantially parallel to the width direction of the circular belt 61 exists outside the upper formation piece 76. This can prevent two containers 100 oriented such that the axial direction of these containers 100 is substantially parallel to the width direction of the circular belt 61 from being placed on the placement member 64.

Alternatively, the length of the one end (the side along the circular belt 61) of the first inclined surface 76a according to the present invention may be appropriately set in consideration of increasing ease of placing on the first inclined surface 76a a single container 100 oriented such that the axial direction of this container 100 is substantially parallel to the width direction of the circular belt 61.

That is, the length of the one end of the first inclined surface 76a is set to such a length that the container 100 can be shaken off when this container 100 is in a state in which part of the container 100 including one of the end portions and having a length equal to or larger than a half the length in the axial direction (referred to as a "half-or-larger part" hereafter) projects outwards from the first inclined surface 76a. For this, it is sufficient that the center of gravity g be positioned outside the first inclined surface 76a when the half-or-larger part of the container 100 projects outwards from the upper formation piece 76.

Accordingly, when the length of the container 100 in the axial direction is X, a length Y of the one end of the first inclined surface 76a is preferably satisfies the following condition:

$$(X-L)/2 < Y < 2(X-L)$$

where X>Y.

In the case where the length Y of the one end of the first inclined surface 76a satisfies the above-described condition, the center of gravity g is positioned outside the first inclined surface 76a when the half-or-larger part of the container 100 projects outwards from the first inclined surface 76a. Thus, the container 100 can be shaken off when this container 100 projects outwards from the first inclined surface 76a by equal to or larger than half the length thereof in the axial direction. Furthermore, when the center of gravity g is positioned on the first inclined surface 76a, the central portion of the container 100 in the axial direction is positioned on the first inclined surface 76a. Accordingly, the container 100 can be held in a stabilized orientation.

The lower formation piece 77 has a substantially rectangular parallelepiped shape and is removably secured to the holding plate 66 with screws. This lower formation piece 77 has a first surface 77a in contact with the other flat plane of the holding plate 66. The first surface 77a of the lower formation piece 77 has a rectangular shape that is substantially the same as that of the other flat surface of the holding plate 66. Furthermore, a projection 79 which projects downwards on the outward leg of the circular belt 61 is provided on the opposite side of the lower formation piece 77 to the first surface 77a.

The projection 79 is formed by obliquely cutting an opposite corner portion of the lower formation piece 77 to the circular belt 61 side and has a lower inclined surface 79a. This lower inclined surface 79a extends from the opposite surface of the lower formation piece 77 to the circular belt 61 side to the surface of the lower formation piece 77 on the circular belt 61 side. Accordingly, the projection 79 is an acute corner portion projecting downwards on the outward leg of the circular belt 61. The distal end of the projection 79 is rounded to have an arc shape.

On the outward leg of the circular belt 61, a smallest distance between a line perpendicular to the circular belt 61, the line being a tangent to the neck portion 102 of the container 100 placed on the placement member 64, and the distal end of the projection 79 of another placement member 64 positioned immediately upstream of the one of the placement members 64 is defined as a gap distance H (see FIG. 8). According to the present embodiment, the gap distance H is set to be larger than the outer diameter D of the neck portion 102 of the container 100 and equal to or smaller than twice the outer diameter D of the neck portion 102 (D<H≤2D).

In the case where the length of the gap distance H is equal to or larger than the outer diameter D of the neck portion 102 (H≤D), the projection 79 of the lower formation piece 77 may interfere with the container 100 placed on the placement member 64 positioned immediately downstream of the placement member 64 that includes this lower formation piece 77. In this case, the orientation of the container 100 placed on the first inclined surface 76a is not stabilized, and the container 100 drops from the first inclined surface 76a (placement member 64).

Furthermore, even when the length of the gap distance H is smaller than the outer diameter of the neck portion 102, on the outward leg of the circular belt 61, the projection 79 of the lower formation piece 77 does not necessarily interfere with the container 100 placed on the first inclined surface 76a of the placement member 64 positioned immediately downstream. However, also in this case, when the placement member 64 is displaced along the upper curved portion of the circular belt 61, the projection 79 of this placement member 64 is brought into contact with the container 100 placed on the placement member 64 positioned immediately downstream. As a result, the container 100 is flicked out of the first inclined surface 76a and drops from the placement member 64.

1-4. Effects of the Container Supply Units

Next, operation of the container ejection part 33 is described with reference to FIGS. 9 and 10.

Figure 9:
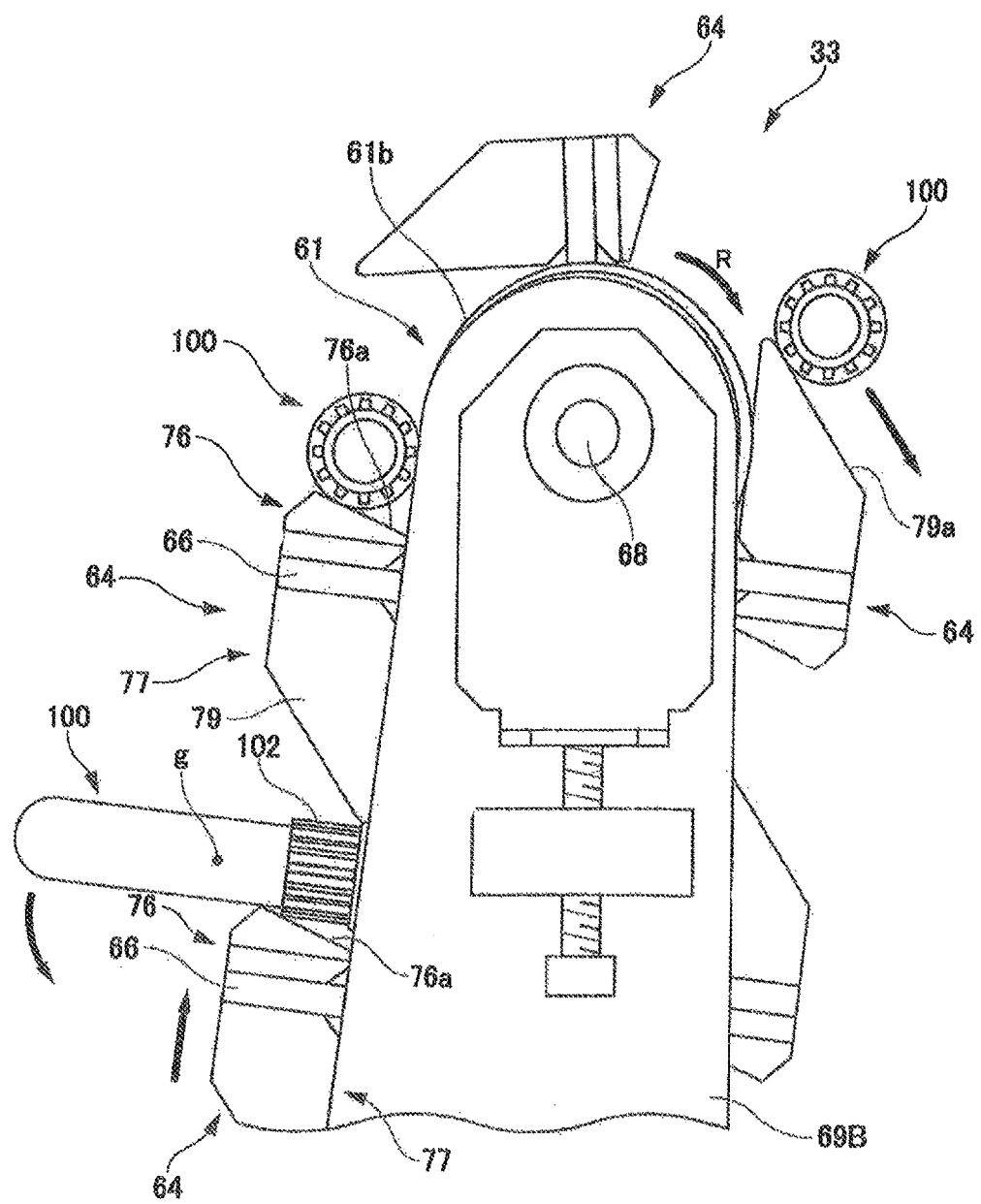
FIG. 9 is an explanatory view illustrating effects of upper portions of placement members of the container supply unit according to the embodiment of the present invention.

FIG. 9 illustrates effects of the upper formation pieces 76 of the placement members 64 of the container ejection part 33. FIG. 10 illustrates effects of the lower formation pieces 77 of the placement members 64 of the container ejection part 33.

As described above, when the circular belt 61 is rotated in the R direction by the belt rotation mechanism 63 (see FIG. 3), the placement members 64 move upwards on the outward leg of the circular belt 61. The plurality of containers 100 stored in the container storage part 32 move onto the plurality of placement members 64.

When the axial direction of the containers 100 having moved onto the placement members 64 is substantially parallel to the width direction of the circular belt 61, the containers 100 are easily placed on the first inclined surfaces 76a of the placement members 64. When the containers 100 oriented such that the axial direction of thereof is substantially parallel to the width direction of the circular belt 61 are placed on the first inclined surfaces 76a of the placement members 64, these containers 100 are brought into contact with the outer circumferential surface 61b of the circular belt 61. Thus, the orientation of the containers 100 can be stabilized in a state in which the axial direction of the containers 100 is substantially parallel to the width direction of the circular belt 61.

The container 100 placed on the placement member 64 while being oriented such that the axial direction thereof is substantially parallel to the width direction of the circular belt 61 moves downwards due to its own weight when the placement member 64 reaches an uppermost portion of the upper curved portion of the circular belt 61. Consequently, the container 100 is guided to the lower inclined surface 79a of the placement member 64 positioned immediately upstream and drops on the alignment rail structure 45 in the cover member 39 while being oriented such that the axial direction of this container 100 is substantially parallel to the width direction of the circular belt 61.

As illustrated in FIG. 3, the two flat plates 51A and 51B of the alignment rail structure 45 are substantially parallel to the width direction of the circular belt 61. Accordingly, the body portion 101 of the container 100 oriented such that the axial direction thereof is substantially parallel to the width direction of the circular belt 61 easily passes through a space between the two flat plates 51A and 51B.

The axial direction of the container 100 the body portion 101 of which has passed through the space between the two flat plates 51A and 51B is parallel to the up-down direction, and the container 100 is held by the alignment rail structure 45 while being oriented such that the bottom portion of these container 100 is positioned on the lower side. The container 100 is guided by the alignment rail structure 45 so as to move to the transfer position. Accordingly, the container 100 ejected to the container alignment part 34 is preferably oriented such that the axial direction thereof is substantially parallel to the width direction of the circular belt 61.

In contrast, the body portions 101 of the containers 100 oriented such that the axial direction thereof is not substantially parallel to the width direction of the circular belt 61, for example, the axial direction thereof is substantially perpendicular to the width direction of the circular belt 61, do not easily pass through the space between the two flat plates 51A and 51B. As a result, jamming of the containers 100 easily occurs in the alignment rail structure 45 in the cover member 39. Accordingly, an orientation in which the axial direction is not substantially parallel to the width direction of the circular belt 61 is an anomalous orientation of the containers 100 ejected from the container ejection part 33.

As illustrated in FIG. 9, when the container 100 which is oriented such that the axial direction of the container 100 is substantially perpendicular to the width direction of the circular belt 61 moves onto the first inclined surface 76a of the placement member 64, the center of gravity g of the container 100 exists outside the first inclined surface 76a. Thus, the container 100 oriented such that the axial direction thereof is substantially perpendicular to the width direction of the circular belt 61 drops from the upper formation piece 76 (placement member 64) on the outward leg of the circular belt 61. Accordingly, anomalous orientations of the containers 100 ejected from the container ejection part 33 can be suppressed in advance.

It is thought that, when the container 100 oriented such that the axial direction thereof is substantially perpendicular to the width direction of the circular belt 61 drops from the placement member 64 on the outward leg of the circular belt 61, the neck portion 102 of the container 100 is caught by the projection 79 of the placement member 64 positioned immediately upstream. However, when the placement member 64 positioned immediately upstream reaches the upper curved portion of the circular belt 61, the projection 79 (lower formation piece 77) is displaced in a direction separating from the circular belt 61. Thus, the container 100 drops from the placement member 64 before the container 100 is ejected to the container alignment part 34.

Figure 10:
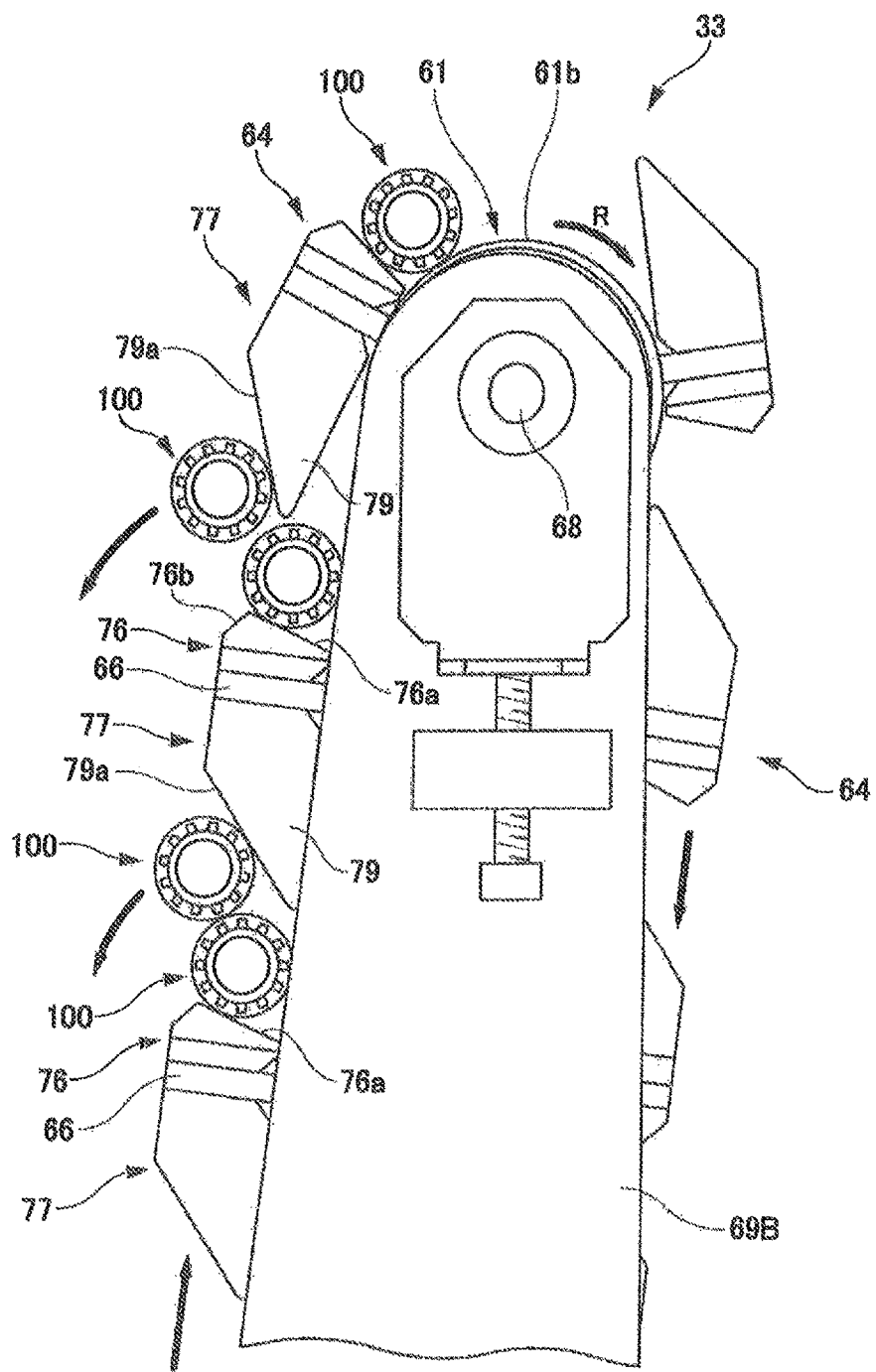
FIG. 10 is an explanatory view illustrating effects of lower portions of the placement members of the container supply unit according to the embodiment of the present invention.

As illustrated in FIG. 10, on the outward leg of the circular belt 61, above the upper formation pieces 76 of the placement members 64, the projections 79 of the placement members 64 positioned immediately upstream are positioned. Furthermore, the lower inclined surfaces 79a of the projections 79 are inclined towards the circular belt 61. Thus, the lower inclined surfaces 79a guide the containers 100 to the upper formation pieces 76 of the placement members 64 positioned immediately downstream. As a result, the containers 100 are easily placed on the placement members 64.

Furthermore, on the outward leg of the circular belt 61, when the containers 100 oriented such that the axial direction thereof is substantially perpendicular to the width direction of the circular belt 61 are placed on the placement members 64, the projections 79 of the placement members 64 positioned immediately upstream are positioned above the containers 100. Thus, spaces that allow the other containers 100 to move thereinto are not formed above the containers 100 placed on the placement members 64.

Accordingly, the other containers 100 cannot be placed on the containers 100 placed on the placement members 64. As a result, the occurrence of a situation in which two containers 100 stacked one on top of the other are ejected from the container ejection part 33 can be prevented, and accordingly, the anomalous orientations of the containers 100 ejected from the container ejection part 33 can be suppressed in advance.

When the other containers 100 move onto the containers 100 placed on the placement members 64, the other containers 100 are brought into contact with the lower inclined surfaces 79a of the projections 79 and drop due to their own weights.

Furthermore, when the placement members 64 reach the upper curved portion of the circular belt 61, the projections 79 of the placement members 64 are displaced in the direction separating from the circular belt 61. At this time, when the other containers 100 move onto top of the containers 100 placed on the placement members 64 positioned immediately downstream, the projections 79 are brought into contact with the other containers 100 and flick the other containers 100. As a result, the occurrence of a situation in which two containers 100 stacked one on top of the other are ejected from the container ejection part 33 can be prevented, and accordingly, the anomalous orientations of the containers 100 ejected from the container ejection part 33 can be suppressed in advance.

The present invention is not limited to the embodiment having been described above and illustrated in the drawings. A variety of modified embodiments are possible without departing from the gist of the invention described in the scope of the claims. For example, according to the above-described embodiment, an example is described in which the automated analyzer is applied to a biochemical analyzer used to analyze biological samples such as blood and urine. However, the automated analyzer according to the present invention is not limited to the above-described embodiment. The automated analyzer according to the present invention can be applied to devices for variety of other analyses such as an analysis of water quality and an analysis of food.

Furthermore, the placement members 64 according to the above-described embodiment each include the holding plate 66, the upper formation piece 76, and the lower formation piece 77. This holding plate 66 is integrally formed with the circular belt 61, and the upper formation piece 76 and the lower formation piece 77 are detachably attached to the holding plate 66. This allows the upper formation piece 76 and the lower formation piece 77 to be easily replaced when the upper formation piece 76 or the lower formation piece 77 is worn or damaged.

Alternatively, the placement member according to the present invention may be formed such that the upper formation piece and the lower formation piece are integrally formed with the holding plate. In this case, the placement member may be detachably attached to the circular belt or integrally formed with the circular belt.

Furthermore, in the container ejection part 33 according to the above-described embodiment, the gap distance H is set to be larger than the outer diameter D of the neck portion 102 of the container 100 and equal to or smaller than twice the outer diameter D of the neck portion 102. Thus, when each of the placement members 64 passes through the upper curved portion of the circular belt 61, the projection 79 of the placement member 64 does not interfere with the container 100 placed on another placement member 64 positioned immediately downstream. Furthermore, when another container 100 exists on the container 100 placed on the placement member 64 positioned immediately downstream, the projection 79 of the placement member 64 passing through the upper curved portion of the circular belt 61 is brought into contact with the other container 100 and flicks the other container 100.

That is, it is sufficient that the projection according to the present invention be provided at such a position that, when the projection passes through the upper curved portion (between the outward leg and the return leg), the projection does not interfere with the container 100 placed on the placement member 64 positioned immediately downstream and flicks the other container 100 existing on the container 100 placed on the placement member 64 positioned immediately downstream.

REFERENCE SIGNS LIST 1 automated analyzer, 2 measurement device, 3 container supply unit, 4 sample holding unit, 5 container carrying unit, 6 sample dispensing unit, 7 reagent thermal-insulation unit, 18 device exterior body, 31 base part, 32 container storage part, 32a, 32b, 32c, 32d side plate, 32e bottom plate, 33 container ejection part, 34 container alignment part, 39 cover member, 45 alignment rail structure, 61 circular belt, 61a inner circumferential surface, 61b outer circumferential surface, 62 belt support mechanism, 63 belt rotation mechanism, 64 placement member, 66 holding plate, 67 drive roller, 68 driven roller, 76 upper formation piece, 76a first inclined surface, 76b second inclined surface, 76c third inclined surface, 76d fourth inclined surface, 77 lower formation piece, 79 projection, 79a lower inclined surface, 100 container, 101 body portion, and 102 neck portion.

The invention claimed is:

1. A container supply unit comprising:
a container storage part in which a plurality of containers are stored;
a container ejection part which ejects the plurality of containers stored in the container storage part; and
a container alignment part which aligns the containers ejected from the container ejection part,
wherein the container ejection part includes
a circular belt,
at least one placement member which is provided on the circular belt and on which the containers are placed, and
a belt rotation mechanism which rotates the circular belt in one direction and which forms an outward leg along which the placement member moves upwards and a return leg along which the placement member moves downwards,
wherein the placement member carries the containers placed thereon on the outward leg and ejects the containers between the outward leg and the return leg to the container alignment part,
wherein an upper portion of the placement member, the upper portion located on an upper side on the outward leg, includes a first inclined surface and a second inclined surface,
wherein the first inclined surface has one end provided on a circular belt side and another end separated from the circular belt, and the first inclined surface is inclined upwards on the outward leg towards the other end, and
wherein the second inclined surface has one end continuous with the first inclined surface and another end separated from the circular belt, and the second inclined surface is inclined downwards on the outward leg towards the other end.

2. The container supply unit according to claim 1, wherein the containers each have a cylindrical shape, and
wherein a length of the first inclined surface intersecting an inclined direction of the first inclined surface is equal to or smaller than lengths of the containers in an axial direction of the containers.

3. The container supply unit according to claim 1, wherein the containers each have a cylindrical shape, and
wherein a length of the first inclined surface in an inclined direction of the first inclined surface is smaller than a length of each of the containers from one end of the container to a center of gravity of the container in an axial direction of the container.

4. The container supply unit according to claim 1, wherein the at least one placement member provided on the circular belt includes a plurality of placement members provided on the circular belt, and
wherein the placement members include projections in lower portions thereof, the lower portions located on a lower side on the outward leg, the projections are displaced relative to the circular belt between the outward leg and the return leg so as to flick the containers placed on the other containers placed on upper portions of the placement members positioned immediately downstream.

5. A container supply unit comprising:
a container storage part in which a plurality of containers are stored;
a container ejection part which ejects the plurality of containers stored in the container storage part; and
a container alignment part which aligns the containers ejected from the container ejection part,
wherein the container ejection part includes
a circular belt,
at least one placement member which is provided on the circular belt and on which the containers are placed, and
a belt rotation mechanism which rotates the circular belt in one direction and which forms an outward leg along which the placement member moves upwards and a return leg along which the placement member moves downwards, wherein the placement member carries the containers placed thereon on the outward leg and ejects the containers between the outward leg and the return leg to the container alignment part, wherein the at least one placement member provided on the circular belt includes a plurality of placement members provided on the circular belt, and wherein the placement members include projections in lower portions thereof, the lower portions located on a lower side on the outward leg, and the projections are displaced relative to the circular belt between the outward leg and the return leg so as to flick the containers placed on the other containers placed on upper portions of the placement members positioned immediately downstream.

6. An automated analyzer which includes a reaction unit which holds containers into which a sample and a reagent are dispensed and a container supply unit which supplies the containers to the reaction unit, wherein the container supply unit includes
a container storage part in which a plurality of containers are stored,
a container ejection part which ejects the plurality of containers stored in the container storage part, and
a container alignment part which aligns the containers ejected from the container ejection part,
wherein the container ejection part includes
a circular belt,
a placement member which is provided on the circular belt and on which the containers are placed, and
a belt rotation mechanism which rotates the circular belt in one direction and which forms an outward leg along which the placement member moves upwards and a return leg along which the placement member moves downwards,
wherein the placement member carries the containers placed thereon on the outward leg and ejects the containers between the outward leg and the return leg to the container alignment part,
wherein an upper portion of the placement member, the upper portion located on an upper side on the outward leg, includes a first inclined surface and a second inclined surface,
wherein the first inclined surface has one end provided on a circular belt side and another end separated from the circular belt, and the first inclined surface is inclined upwards on the outward leg towards the other end, and
wherein the second inclined surface has one end continuous with the first inclined surface and another end separated from the circular belt, and the second inclined surface is inclined downwards on the outward leg towards the other end.

7. An automated analyzer which includes a reaction unit which holds containers into which a sample and a reagent are dispensed and a container supply unit which supplies the containers to the reaction unit, wherein the container supply unit includes
a container storage part in which a plurality of containers are stored,
a container ejection part which ejects the plurality of containers stored in the container storage part, and
a container alignment part which aligns the containers ejected from the container ejection part,
wherein the container ejection part includes
a circular belt,
at least one placement member which is provided on the circular belt and on which the containers are placed, and
a belt rotation mechanism which rotates the circular belt in one direction and which forms an outward leg along which the placement member moves upwards and a return leg along which the placement member moves downwards,
wherein the placement member carries the containers placed thereon on the outward leg and ejects the containers between the outward leg and the return leg to the container alignment part,
wherein the at least one placement member provided on the circular belt includes a plurality of placement members provided on the circular belt, and
wherein the placement members include projections in lower portions thereof, the lower portions located on a lower side on the outward leg, the projections are displaced relative to the circular belt between the outward leg and the return leg so as to flick the containers placed on the other containers placed on upper portions of the placement members positioned immediately downstream.

\* \* \* \* \*